| United States Patent [19] | [11] | 4,347,216 |
|---|---|---|
| Kawasaki et al. | [45] | Aug. 31, 1982 |

[54] WET SAMPLE DECOMPOSING APPARATUS

[75] Inventors: Kazuyoshi Kawasaki; Yasumitsu Katsuno, both of Kitakyushu, Japan

[73] Assignee: Mitsubishi Kasei Kogyo Kabushiki Kaisha, Tokyo, Japan

[21] Appl. No.: 277,197

[22] Filed: Jun. 25, 1981

[30] Foreign Application Priority Data

Jun. 30, 1980 [JP] Japan .................................. 55-88923
Sep. 12, 1980 [JP] Japan ................................ 55-126777

[51] Int. Cl.$^3$ ........................ G01N 31/12; H05B 6/64
[52] U.S. Cl. ................................ 422/78; 23/230 PC;
219/10.55 A; 422/80; 422/102; 422/68
[58] Field of Search ....................... 422/68, 78, 79, 80,
422/102; 23/230 PC, 906; 219/10.55 R, 10.55 A

[56] References Cited

U.S. PATENT DOCUMENTS 3,830,893 8/1974 Steingiser .................... 219/10.55 A
4,015,936 4/1977 Kumazawa ..................... 23/230 PC
4,080,165 3/1978 Abu-Samra et al. .

OTHER PUBLICATIONS

"Wet Ashing of Some Biological Samples in a Microwave Oven", Analytical Chemistry, vol. 47, No. 7, Jul. 1975, pp. 1475-1479.
"Microwave Oven-Based Wet Digestion Technique", Analytical Chemistry, vol. 50, No. 7, Jun., 1978, pp. 1021-1023.
"Multielement Analytical Techniques at the FDA", International Laboratory, Mar./Apr., 1978, pp. 25-38.

Primary Examiner—Michael S. Marcus
Attorney, Agent, or Firm—Oblon, Fisher, Spivak, McClelland & Maier

[57] ABSTRACT

A sample decomposing apparatus of the type which includes a microwave heating containing chamber having on one side thereof a transparent door that intercepts microwaves and a perforation through a wall of the container, a microwave controller for controlling microwave radiated in the microwave heating container, and a gas collector having a gas discharge opening and at least one opening for removably mounting a plurality of sample decomposing containers. The gas collector is disposed in the microwave heating container, and the gas generated in the sample decomposing containers is collected by the gas collector and discharged to outside through the gas discharge opening.

13 Claims, 34 Drawing Figures

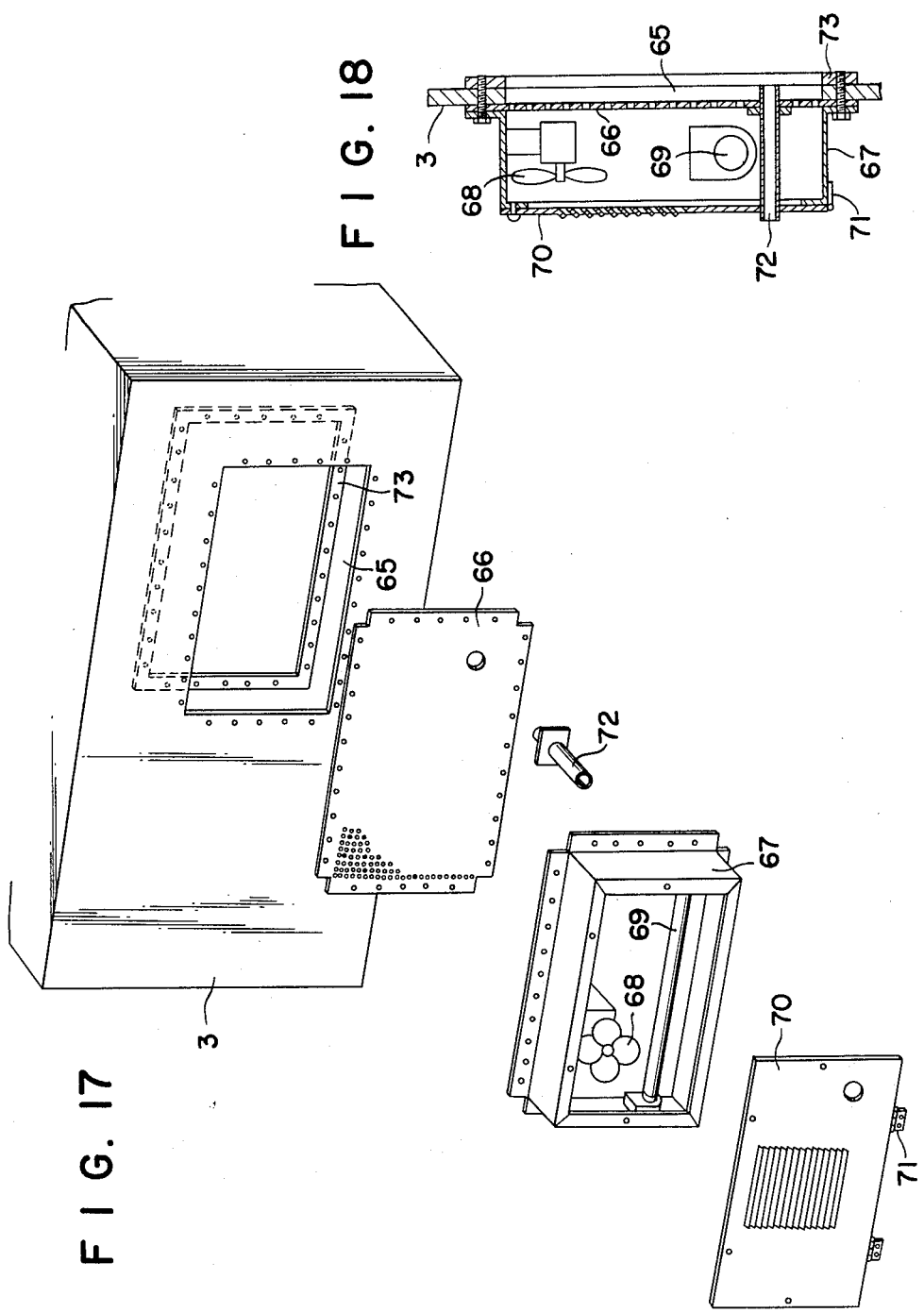

F I G. 25
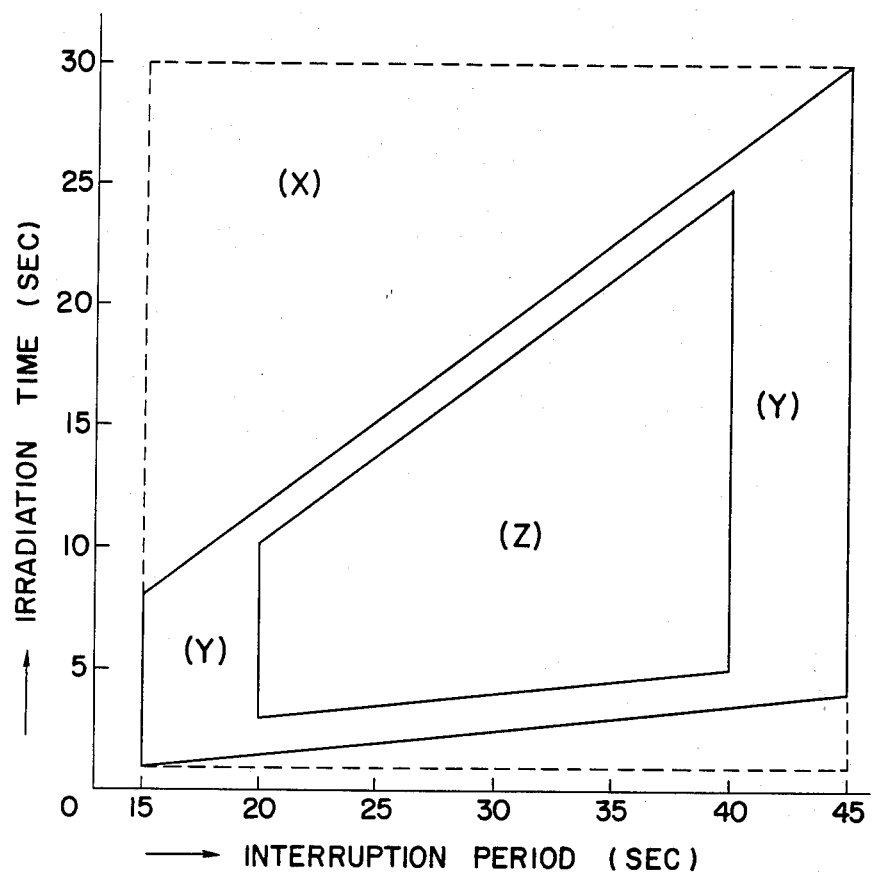

WET SAMPLE DECOMPOSING APPARATUS

BACKGROUND OF THE INVENTION

1. Field of the Invention

This invention relates to sample decomposing apparatus capable of rapidly decomposing or digesting the sample with easy operation by using microwave heating.

2. Description of the Prior Art

To analyze nitrogen component or metal components contained in such samples as coal, petroleum, heavy oil, fertilizer, soil, foodstuff, biological samples, etc., it is necessary to predecompose or digest the sample.

Prior art methods of decomposition include so-called Kjeldahl decomposition method in which such decomposition agent as sulfuric acid, potassium sulfate, copper sulfate and a decomposition catalyst is added to the sample and heated, and methods utilizing sulfuric acid and nitric acid; perchloric acid and nitric acid, respectively. However, these prior art methods are disadvantageous in that it takes a long time of 2 to 10 hours for decomposing the sample as desired.

To decrease the decomposition time, in recent years it has been proposed a method in which a flask containing a sample and a decomposing agent is disposed in a container heated by microwave. This method, however, has such defect that vapor or gas generated from the flask at the early stage of decomposition condenses on the inner wall of the heating container, and that where perchloric acid is used, a white fume of the perchloric acid fills the container, thus making it impossible to inspect the interior thereof. In the wet decomposition of a sample, incapability of inspecting the interior constitutes a fatal defect because foaming or bumping, that is, violent boiling often occurs unless the heating condition at the early heating stage is adequate.

SUMMARY OF THE INVENTION

It is therefore an object of this invention to provide an improved sample decomposing apparatus that can obviate these difficulties.

According to this invention, there is provided a sample decomposing apparatus including a microwave heating container forming a chamber and having on one side thereof a transparent door that intercepts microwaves and a wall having a perforation formed therethrough, a microwave controller for controlling microwaves radiated in the chamber, a plurality of sample decomposing containers, a hollow gas collector having a first gas, discharge opening and a plurality of openings for removably mounting each of the plurality of sample decomposing containers, each of the sample decomposing containers containing a sample to be decomposed to generate the first gas, the hollow gas collector being disposed in the microwave heating container, a mechanism for introducing a second gas into the hollow gas collector from the exterior thereof and an internal suction mechanism for removing the first and second gases from the gas collector through the perforation in the wall of the heating container.

BRIEF DESCRIPTION OF THE DRAWINGS

In the accompanying drawings:

FIGS. 13a through 13d show other examples of the gas collector and the sample decomposing container in which FIG. 13a is a front view, partly broken away; FIG. 13b is a sectional view taken along a line XIIIb—XIIIb shown in FIG. 13a; FIG. 13c is a sectional view taken along a line XIIIc—XIIIc shown in FIG. 13a; and FIG. 13d is a sectional view taken along a line XIIId—XIIId shown in FIG. 13a;

FIGS. 14a–14c show another example of the gas collector in which FIG. 14a is a longitudinal sectional view; FIG. 14b is a plan view; and FIG. 14c is a front view;

FIG. 17 is an exploded rear view showing the apparatus embodying the invention;

FIG. 18 is a vertical sectional view showing an assembled state of the parts shown in FIG. 17;

FIG. 25 is a graph showing the relation between the irradiation time and the interruption period.

DESCRIPTION OF THE PREFERRED EMBODIMENTS

Figure 1:
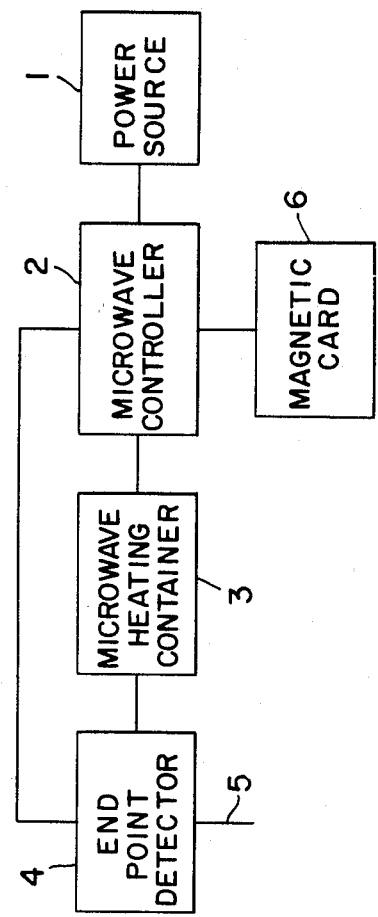
FIG. 1 is a block diagram showing one example of the arrangement of the decomposition apparatus embodying the invention.

Referring now to FIG. 1 showing the block diagram of the sample decomposing apparatus embodying the invention, there are provided a microwave controller 2 including an oscillator (to be described later) energized by a source of power 1 for radiating microwave in a microwave heating container or vessel 3. The microwave dose is controlled by inputting to the microwave controller 2 signals prerecorded on a magnetic card 6 and representing the type and quantity of the sample, the type and quantity of the decomposing agent, etc., and a signal from an end point detector 4. The microwave heating container 3 is provided with a sample decomposing container or vessel (to be described later) containing a sample and a decomposing agent and heated by irradiated microwave for decomposing the sample contained therein. The gas generated in the decomposing container is discharged to the outside through the end point detector 4 and a conduit 5. The end point detector 4 detects the gas generated in the decomposing container to detect the termination of generation of a specific gas or decrease in the temperature of the generated gas, that is completion of the decomposition of the sample so as to send a signal to the microwave controller 2 which stops radiation of the microwave. The gas discharged from the conduit 5 is removed of harmful components by a well known harmful gas remover, not shown.

Figure 2:
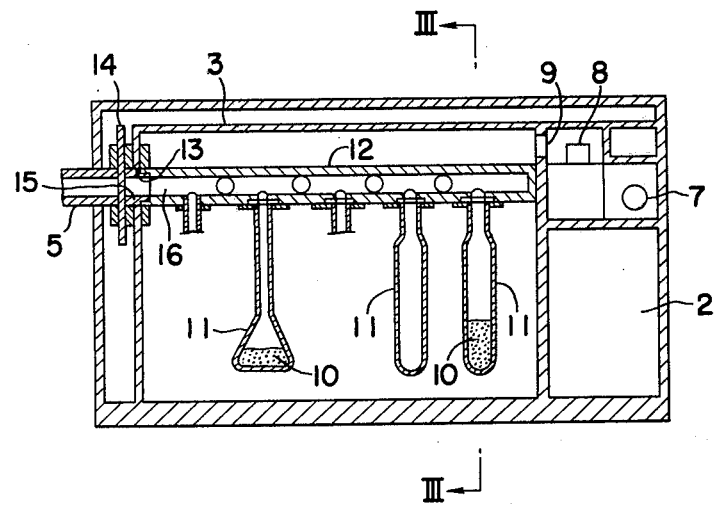
FIG. 2 is a sectional view of the apparatus comprising a microwave heating container, a gas collector and sample decomposing containers.
Figure 3:
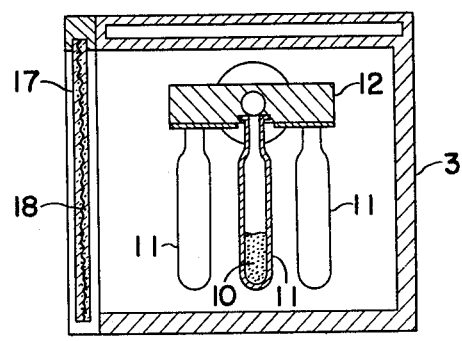
FIG. 3 is a cross-sectional view of the apparatus shown in FIG. 2 taken along a line III—III.

FIGS. 2 and 3 show sample decomposing containers 11 and a gas collector 12, in which reference numerals 2 and 3 designate the same elements as those shown in FIG. 1.

The microwave heating container 3 takes the form of a box constituted by a transparent front door 17 embedded with a metal wirenet 18 that shields or intercepts the microwave and a side wall having a hole 13. In the container 3 is horizontally disposed the gas collector 12 with a conduit 15 threaded into the end opening of the gas collector 12 and passed through the hole 13.

Figure 4:
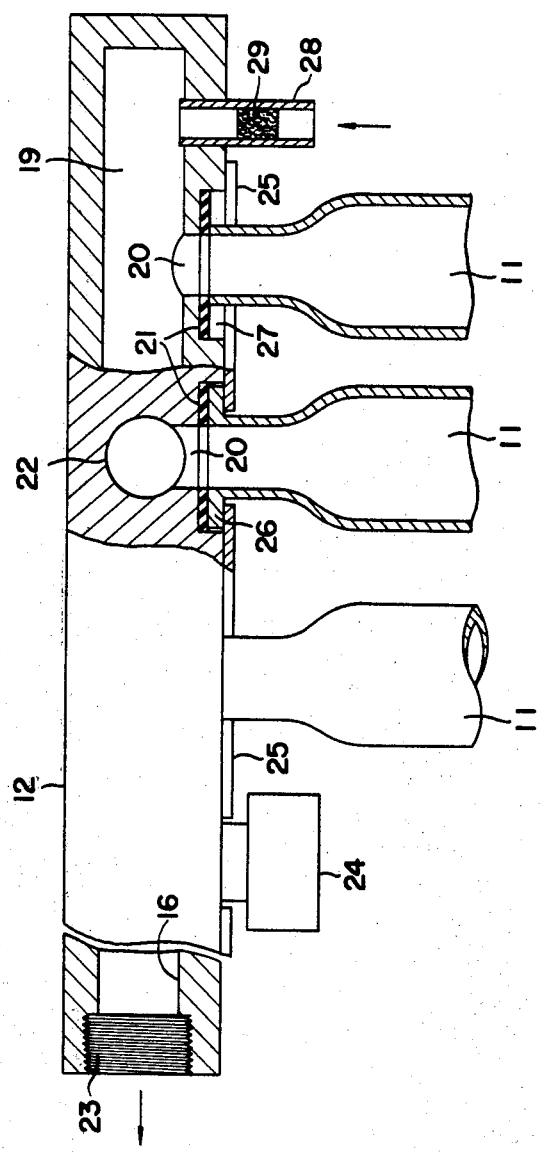
FIG. 4 is side view, partly in section and partly broken away, showing the generated gas collector and the sample decomposition containers.
Figure 5:
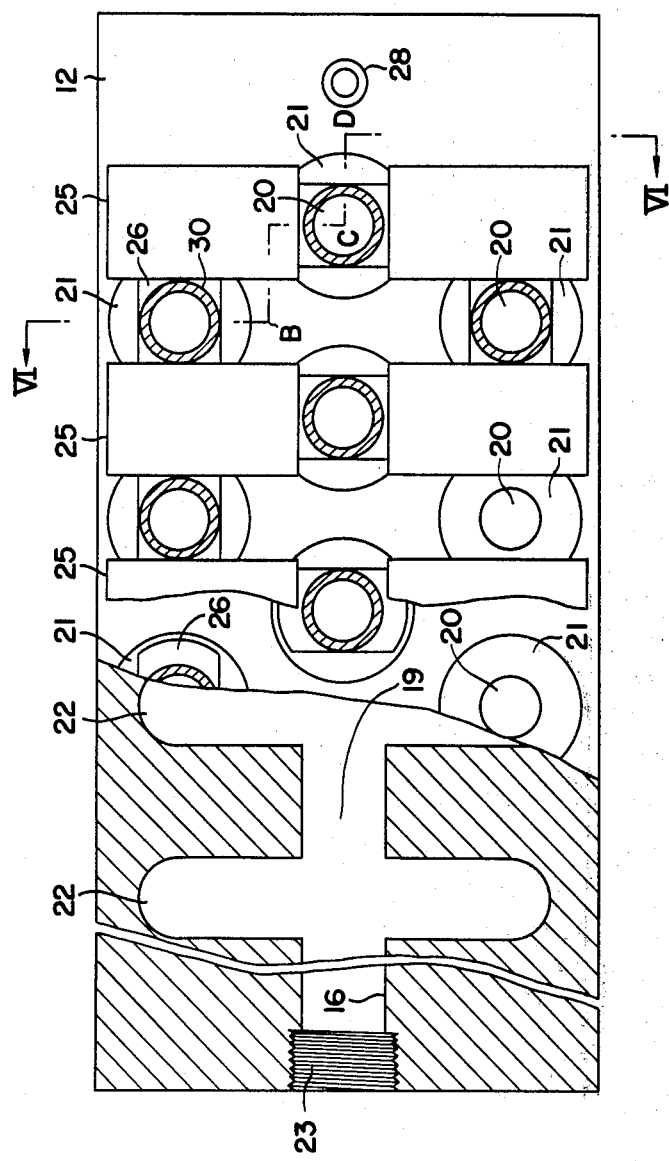
FIG. 5 is a bottom view, partly in section, showing the gas collector and containers shown in FIG. 4.
Figure 6:
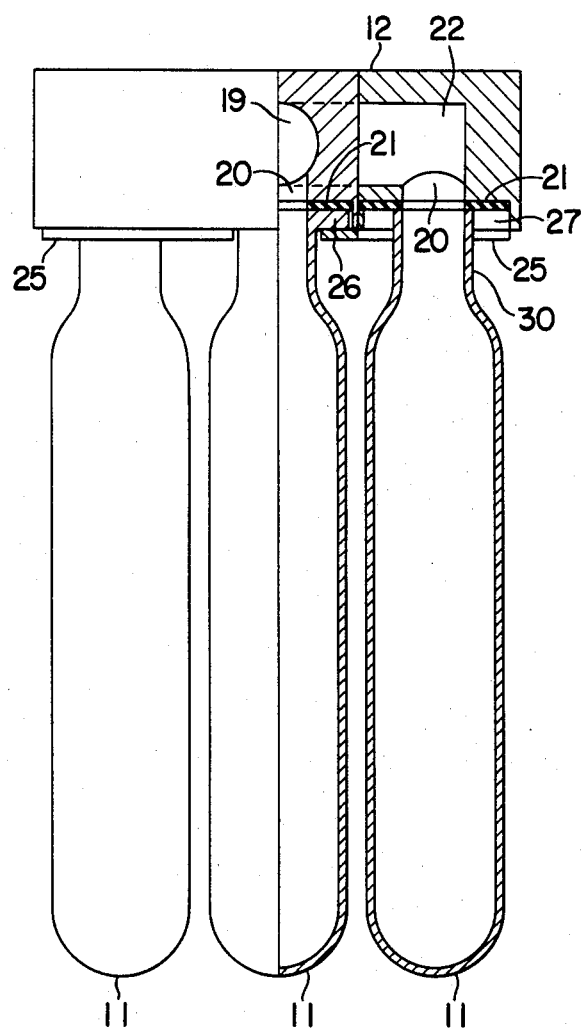
FIG. 6 is a sectional view taken along a line VI—VI passing through points B, C and D shown in FIG. 5.

The purpose of the gas collector 12 is to collect the gas generated in the sample decomposing containers 11 for discharging the collected gas to the outside and to suspend the sample decomposing containers and is made of such material having a small dielectric constant, resistant to the corrosion of the generated gas, resistant to heat and a high mechanical strength as polyamide resin, ethylene fluoride resin, glass, ceramic, etc. As shown in FIGS. 4-6, the gas collector 12 comprises a block having a large wall thickness and openings at both ends. The opening 16 at one end is formed with screw threads 23 for connecting conduit 15, which is cummunicated with a discharge conduit 5 via plate 14 provided with a number of perforations while the opening at the other end is connected to a pipe 28 packed with a filter 29 for introducing clean air. The bottom surface of the gas collector is provided with a plurality of openings 20 for removably mounting the neck portions of the sample decomposing containers 11. These openings are usually formed vertically or obliquely through the bottom wall of the gas collector 12, but may be formed through the side wall of the gas collector. These openings are formed at a proper spacing permitting easy mounting and dismounting of the sample decomposing containers. Staggered arrangements of these openings 20 as shown in FIG. 5 facilitate ready mounting, dismounting and supervision of the sample decomposing containers and ensure uniform irradiation of the microwave. However, these openings may also be arranged in the form of a lattice. In the illustrated example, the openings 20 are connected with gas inlet and outlet openings through flow passages 19 and 22 in the gas collector 12.

Each opening 20 is formed with a concentric recess 27 of a size sufficient to accommodate the flange 26 of a sample decomposing container 11 and a packing 21 is held in the recess 27 by a rectangular cover plate 25 so as to removably mount the sample decomposing container with a bayonet coupler. It is advantageous to make the packing 21 of heat and corrosion resistant material, for example, a composite circular sheet made up of an elastic sheet made of fluorine rubber or the like interposed between sheets of tetrafluoroethylene resin. Cover plates 25 support the lower surfaces of the flanges 26 when the necks of the sample decomposing containers 11 are mounted in the recesses 27.

Each sample decomposing container 11 is a top opened cylindrical container having a flange 26 at the top clamped by the cover plate 25 and is made of such material as borosilicate glass or quartz glass that transmits microwave, not corroded by the decomposing agent and is transparent permitting visual inspection of the interior of the container. Cylindrical containers are preferred from the standpoint of space economy. Bulb shaped containers, messflasks and triangular flasks capable of increasing the surface area of the liquid to be decomposed are advantageous because they can decrease the decomposition time of the sample. The flange 26 may take any form so long as it can engage the cover plate 25 after inserting the top portion into the recess 27 and then rotating the container. For example, as shown in FIG. 7c and 8c a plate having a crowned lower surface 32 is advantageous.

Figure 7A:
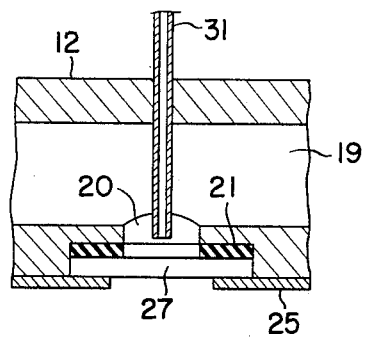
FIGS. 7a, 7b and 7c and FIGS. 8a, 8b and 8c show methods of mounting the sample decomposing container.
Figure 8A:
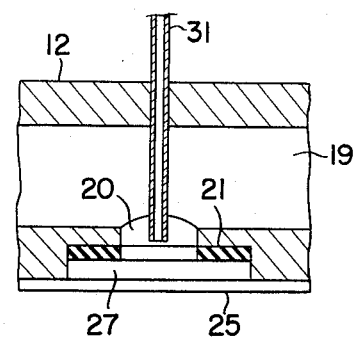
Figure 7B:
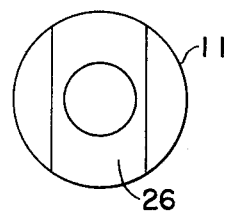
Figure 8B:
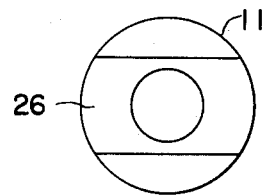
Figure 7C:
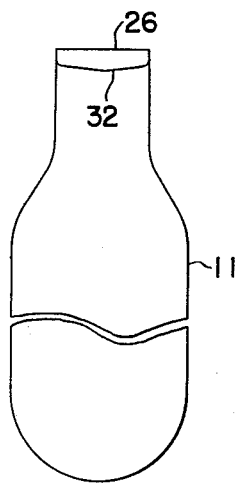
Figure 8C:
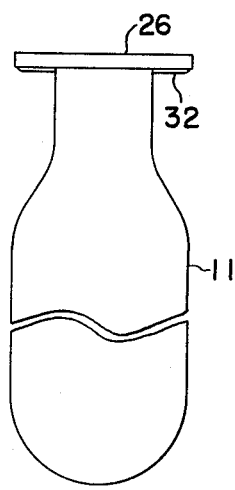

The sample decomposing container 11 is attached to the gas collector 12 such that, when the cover plate 25 is held at a position shown in FIG. 7a, the flange 26 is brought to the position shown in FIG. 7b, whereas when the cover plate is held in a position shown in FIG. 8a (representing a side view of FIG. 7a), the flange 26 is brought to a position shown in FIG. 8c, then the flange 26 is inserted into the recess 27 and rotated approximately 90° C. Dismounting of the container is done in a reverse order. When the number of samples is small, not used opening 20 is closed by a sealing plug 24 as shown in FIG. 4. Provision of pipes 31 above the opening 20 of the gas collector as shown in FIGS. 7a and 8a faciliates addition of a decomposing agent or the like.

Figure 9:
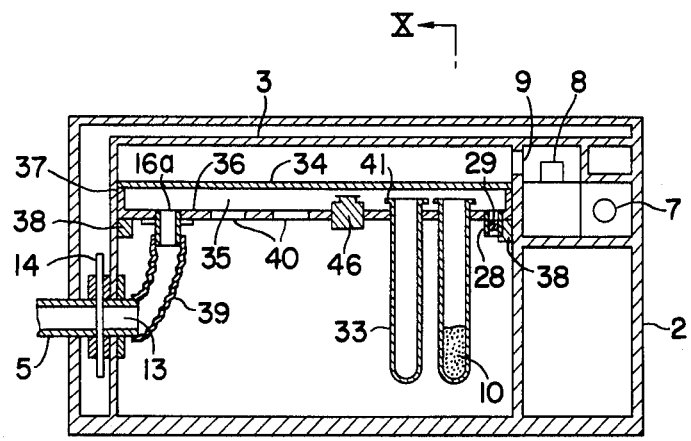
FIG. 9 is a sectional view showing a modified embodiment of the generated gas collector and the sample decomposing containers embodying the invention.
Figure 10:
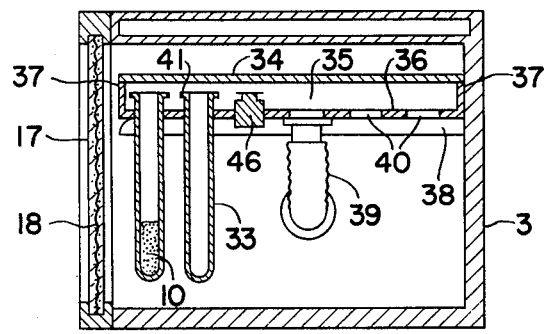
FIG. 10 is a sectional view taken along a line X—X in FIG. 9.
Figure 11:
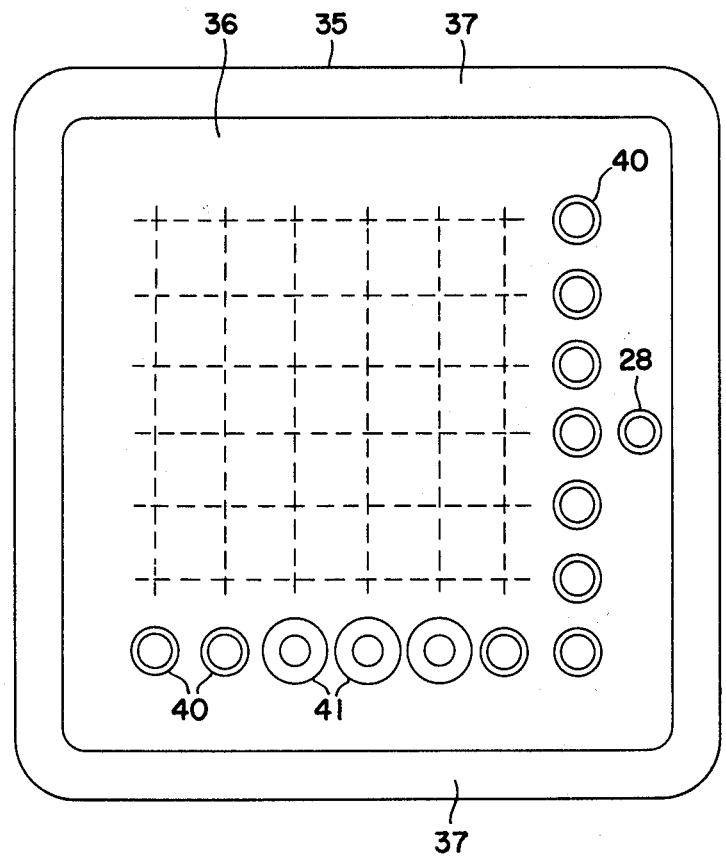
FIG. 11 is a plan view showing the arrangement of the gas collector and the sample decomposing container shown in FIG. 10.

FIGS. 9 through 11 illustrate another embodiment of this invention comprising a gas collector 35, and sample decomposing containers 33. The other elements are designated by the same reference numerals as in FIGS. 1 to 3.

The gas collector 35 is constituted by a container or vessel 36 and a lid 34 which are made of the same material as the gas collector 12 described above. A gas discharging port 16a is provided for one end of the container 36 while a clean air admitting pipe 28 packed with a filter is connected to the other end. The bottom plate of the container 36 is formed with a plurality of openings 40 for mounting the sample decomposing containers 33. Openings 40 are spaced from each other sufficient to readily mount and dismount the sample decomposing containers. In this embodiment, the openings 40 are arranged in the form of a grid as shown in FIG. 11, but it is advantageous to form each opening 40 to have a funnel shape with its surface covered with a slidable sleeve made of fluorinated ethylene resin or the like to facilitate mounting and dismounting of the sample decomposing container.

After mounted with the sample decomposing containers 33, the container 33 is inserted between the lid 34 horizontally mounted in the upper portion of the microwave heating container 3 and supports 38 on both sides thereof and maintained in an air tight state by sliding surfaces 37 between opposite side surfaces of the lid 34 and the peripheral surface of the container 36. The gas discharge opening 16a is connected to the discharge opening 13 via a flexible pipe 39.

Each of the sample decomposing container 33 is a cylindrical container with one end opened and has an outer diameter suitable for removably fitting into the opening 40 and made of the same material as the sample decomposing container 11 described above. Where a flange 41 is secured to the opening of the container 33, its mounting and dismounting become easy, and when the outer diameter of the sample decomposing container 33 is slightly smaller than the diameter of the opening 40, the flange 41 is used to suspend the container 33. Usually, the upper portion of the container 33 is bulged outwardly to conform to the contour of the opening 40. By coating the bulged out portion with a smooth film of fluorinated ethylene resin, for example, not only the mounting and dismounting of the container 33 are facilitated but also air tightness is improved. Where a pouring port is provided for the opening of the container 33, decomposed liquid can be readily transferred to another container.

When the number of the samples to be decomposed is small, not used opening 40 is closed by a sealing plug 46 inserted from above. To prevent the sealing plug from disengaging when the pressure in the gas collector is rapidly reduced by an exhaust fan, not shown, it is advantageous to made the plug of heavy material such as borosilicate glass.

Figure 12:
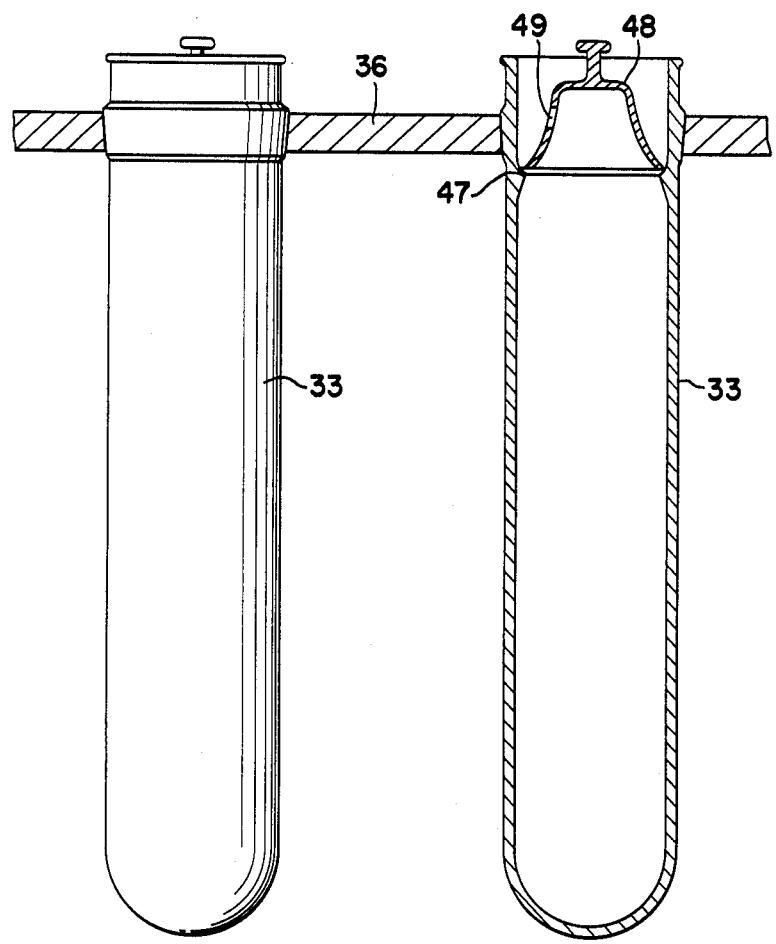
FIG. 12 is a side view, partly in section, showing the sample decomposing container utilized in the gas collector shown in FIG. 11.

FIG. 12 shows one example of the construction of the sample decomposing container 33 shown in FIGS. 9–11, in which the inner diameter of the upper portion of the container 33 is reduced to form a shoulder 47 and a bell shaped cap 48 having an outer diameter smaller than the inner diameter of the container is mounted on the shoulder 47. The side wall of the cap 48 is provided with an opening 49 for discharging gas evolved as a result of decomposition.

The sample decomposing container 33 shown in FIG. 12 can prevent spattering of the sample even when it bumps and collect the mist of the decomposition agent by the cap 48 so that it is possible to decrease the quantity of the decomposition agent as well as the measurement error caused thereby.

Moreover, as the bell shaped cap 48 makes a line contact with the shoulder 47 it is not only possible to prevent stay of the decomposition agent and sample at the contact and between the cap 48 and the inner wall of the container 33 thus preventing combustion of the staying material due to overheating.

FIGS. 13a through 13d show another example of the gas collector and the decomposing container. The gas collector 50 is formed as a rectangular bar having an inner gas passage 51 and made of the same material as the gas collectors 12 and 35 and one side wall thereof is provided with a tapered opening 52 whose cross-sectional area increases toward outside. A sample decomposing container 53 takes the form of an inverted letter L and its gas discharge conduit 54 is air tightly fitted in the tapered opening 52. Although it is advantageous to dispose the gas discharge conduit 54 substantially at right angles with respect to the sample decomposing container to facilitate handling thereof, the conduit 54 may be disposed at other angles. Usually, the gas discharge conduit 54 is provided near the upper end of the sample decomposing container 53, but depending upon the application it may be provided near the axial center of the container 53.

The sample decomposing container 53 can readily be attached to the gas collector 50 by merely inserting the gas discharge conduit 54 into the tapered opening 52 in an air tight fashion. Since the sample decomposing container 53 is secured to the gas collector 50 on the outside thereof any container 53 having different shape can be combined.

Figure 13A:
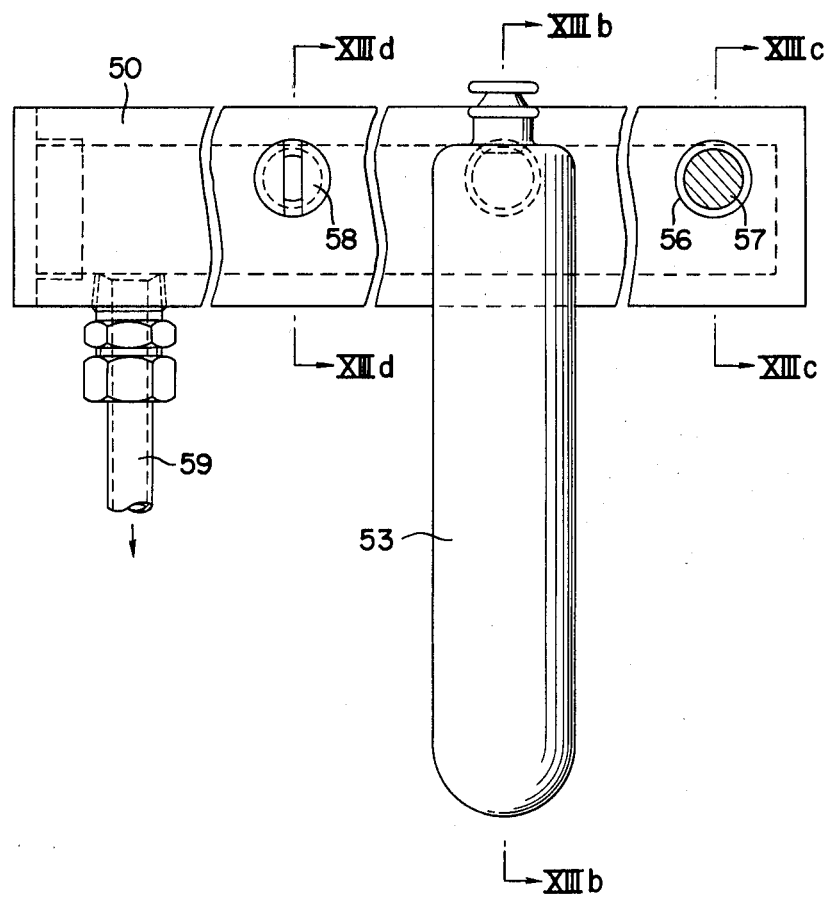
Figure 13B:
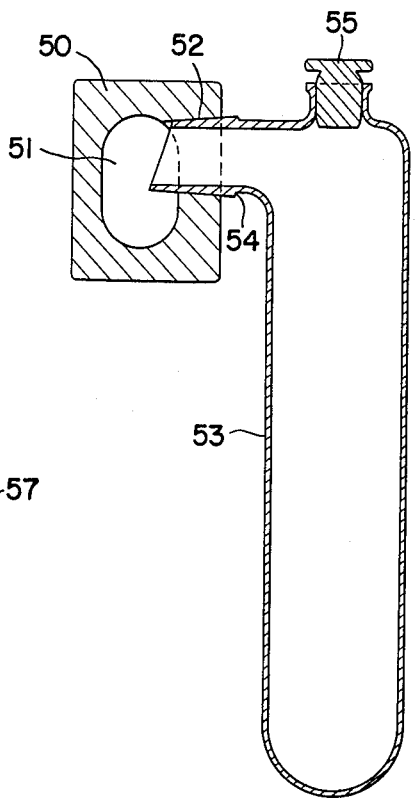

As shown in FIG. 13b, a plug 55 is provided at the upper end of the container 53 for introducing a decomposing agent or the like.

Figure 13C:
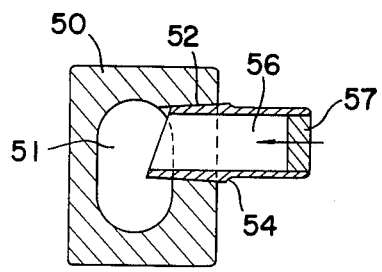
Figure 13D:
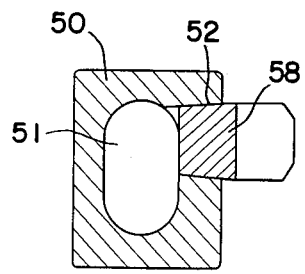

FIGS. 13c and 13d show a conduit 56 packed with a filter 57 for introducing clean air into the gas collector 50 and a sealing plug 58 fitted to the tapered opening 52 when neither of the sample decomposing container and the air filtering conduit 51 is used.

Figure 14A:
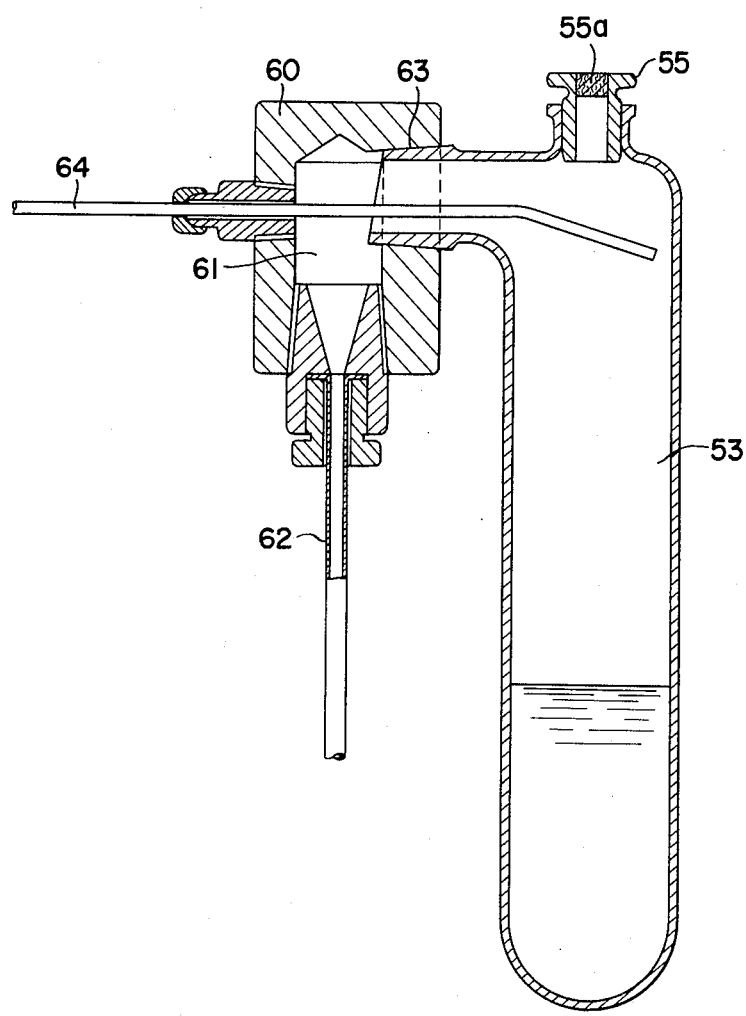
Figure 14B:
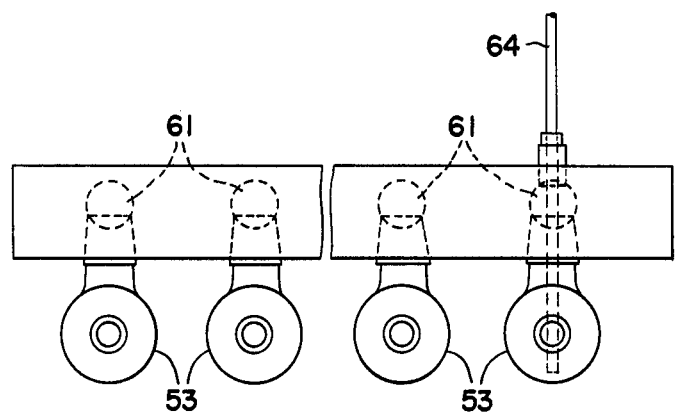
Figure 14C:
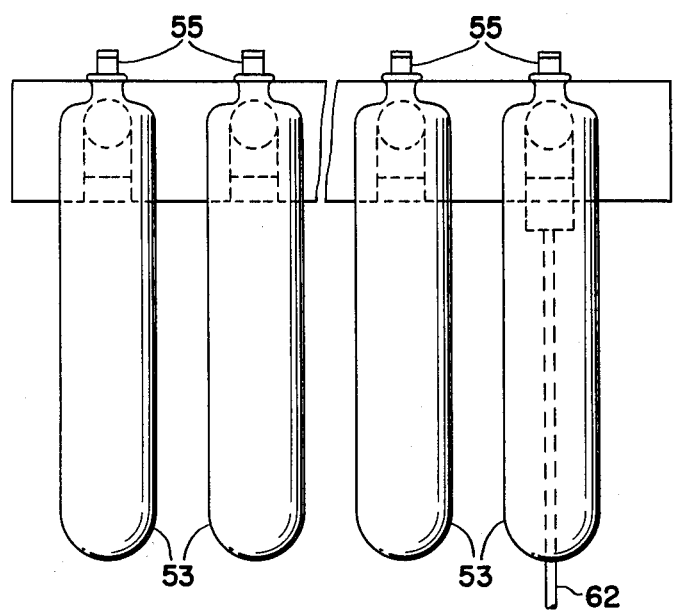

FIGS. 14a through 14c show another example of the gas collector where the sample decomposing container 53 shown in FIG. 13b is used. In this example, gases generated in respective sample decomposing containers 53 are taken out through independent gas flow passages 61 in the gas collector 60. More particularly, each gas flow passage 61 is connected to a gas discharge conduit 62. A pouring tube 64 is provided for one side of the gas collector 60 on the side opposite a tapered opening 63 for pouring a decomposing agent or the like into the container 53 at any desired time during decomposition. Further, in this example, clean air is introduced into the container 53 through a filter 55a packed in a plug 55 at the top of the container 53.

Figure 15:
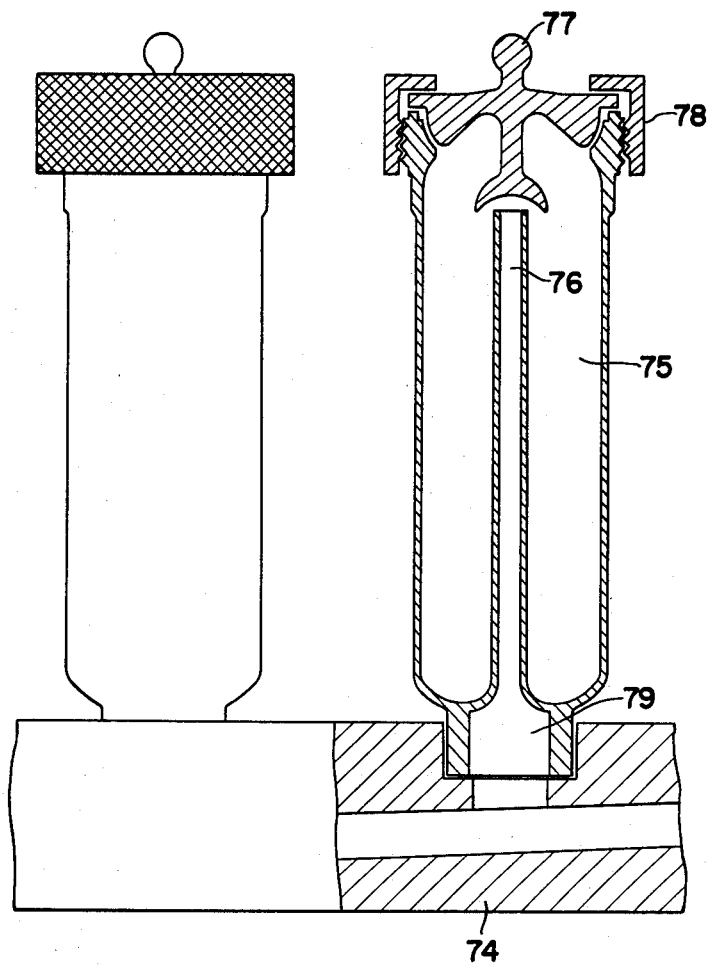
FIGS. 15 and 16 are front views, partly in section, showing other examples of the gas collector and the sample decomposing container.
Figure 16:
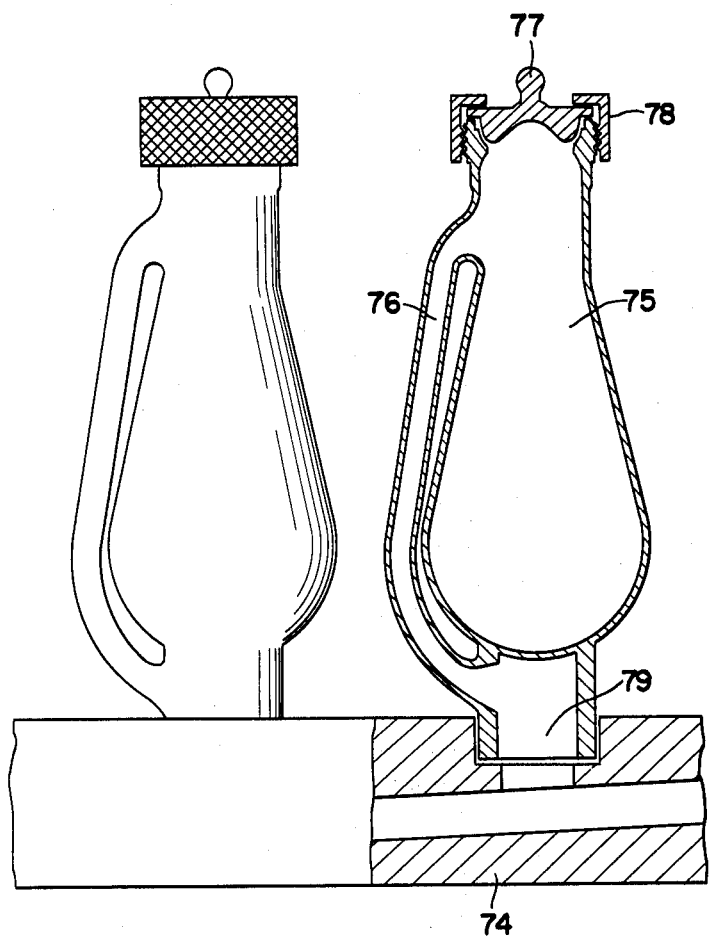

FIGS. 15 and 16 illustrate still other examples of the gas collector and the sample decomposing container. Thus, the gas collector 74 is provided with upwardly directed openings 79 for mounting sample decomposing containers 75. The gas collector 74 is disposed in the lower portion of the microwave heating container 3 (see FIG. 2) and the sample decomposing containers 75 are fitted into openings 79 from above. Each sample decomposing container 75 is constructed such that the gas generated therein is discharged through the bottom thereof into the gas collector 74. To this end, a pipe 76 extending to the upper portion of the container is provided. The upper opening of the container 75 is hermetically sealed by a cap 77 clamped by a knurled clamping member 78 threaded to the top of the container. In the modification shown in FIG. 16, the gas discharge pipe 76 is provided on the outside of the container 75.

With the embodiments shown in FIGS. 15 and 16, mounting and dismounting of the sample decomposing containers onto and from the gas collector are easy. Moreover, there is an advantage that contamination caused by gas from adjacent sample decomposing container can be prevented.

FIG. 17 is an exploded rear view of the apparatus of this invention. More particularly, a portion of a side of the microwave heating container 3 opposite to the side provided with the door 17 (see FIG. 3) is removed to form an opening 65 for incorporating various component elements. More particularly, a shielding metal plate 66 provided with a large number of perforations is secured to close the opening 65 to prevent leakage of the microwave. On the outside of the shielding plate 66 is secured a frame 67 for supporting an exhaust fan 68, a fluorescent lamp 69, etc. The exhaust fan is provided for the purpose of adjusting the temperature in the microwave heating container 3 or exhausting gas generated at the time of decomposing the sample and leaks into the container 3. The lamp 69 is used to inspect or supervise the state of the sample in the container during decomposition. When the state is supervised through the window 17 the light emitted from the lamp 69 illuminates the sample and then passes through the window so that the supervision becomes easy. The perforated plate 66 releases pressure caused by an accidental explosion which may occur at the later stage of the decomposition when perchloric acid or the like is used as the decomposing agent by disengaging a pressure relief plate 70 from the frame 67. The pressure relief plate 70 is secured to the frame 67 with hinges 71 such that it can be opened with relatively low pressure.

FIG. 18 shows a vertical sectional view showing the frame 67 and elements supported thereby. It is advantageous to provide a bulkhead union 72 for passing a conduit connected to the gas discharge opening of gas collector 12, 35, 50 or 60, and a conduit 31 or 64 for incorporating a decomposing agent or the like.

Figure 19:
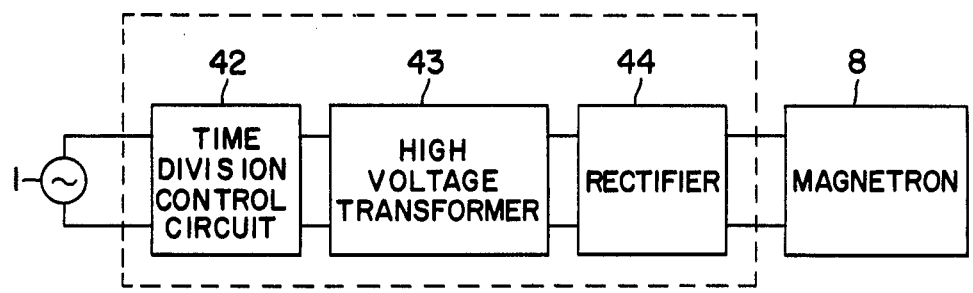
FIG. 19 is a block diagram showing a microwave controller.
Figure 20:
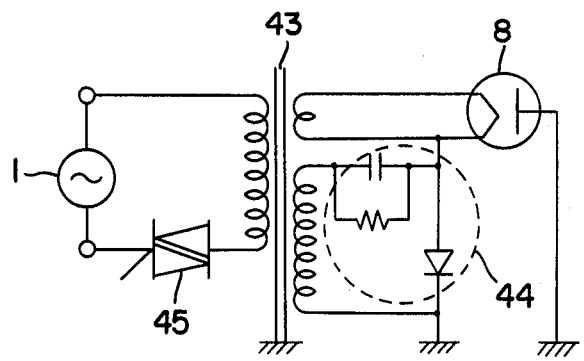
FIG. 20 shows an electric connection of said microwave controller.

With reference to FIGS. 19 and 20, one example of the microwave controller 2 will be described. It comprises a pulse width control circuit 42, a high voltage transformer 43 and a rectifier 44. More particularly, a triac element 45 is used as the pulse width control circuit 42 for interrupting current supplied from source 1 so as to control the quantity of the microwave generated by a magnetron tube 8 to a desired value. After converting by the transformer 43 into high voltage current, the output of the triac 45 is rectified by the rectifier 44 and then impressed upon the anode electrode of the magnetron tube 8 to cause it to act a microwave oscillator. Since, this controller 2 controls the radiated quantity of the microwave on the time division basis, bumping of the sample caused by overheating can be efficiently prevented where the number of the samples is small.

The decomposition of a sample with the apparatus described above is performed in the following manner. A predetermined quantity of a sample 10 and a decomposing agent is put in each of the sample decomposing container 11, 33 or 53 and then the container is attached to the gas collector 12, 35, 50 or 60. An exhaust fan (not shown) connected to conduit 5 is operated to suck clean air through filter 29 packed in pipe 28. The air thus cleaned flows through a passage 19 in the gas collector 12, or the air passage in the gas collector 35 and finally discharged to the outside of the apparatus through the microwave shielding plate 14, end point detector 4 and the conduit 5. Then, the microwave controller 2 is operated to cause the magnetron tube 8 to generate microwave which is radiated into the microwave heating container 3 to begin heating of the sample. The magnetron tube 8 is cooled by the fan 7. The quantity of the microwave radiated is controlled by adjusting the pulse width control circuit 42 while visually observing the heating state of the sample in the sample decomposing container 11 or 33. The gas (also containing vapor of acid) generated in the sample decomposing container enters into the flow passage 19 of the gas collector 12 or the flow passage in the collector 35 and finally discharged to the outside together with the air. Completion of the decomposition is detected by the end point detector 4 or visually observing the interior state of the sample decomposing container and then stopping the operation of the microwave controller 2. The decomposed sample is analyzed by an appropriate analyzer after dismounting the sample decomposing container from the gas collector.

Figure 21:
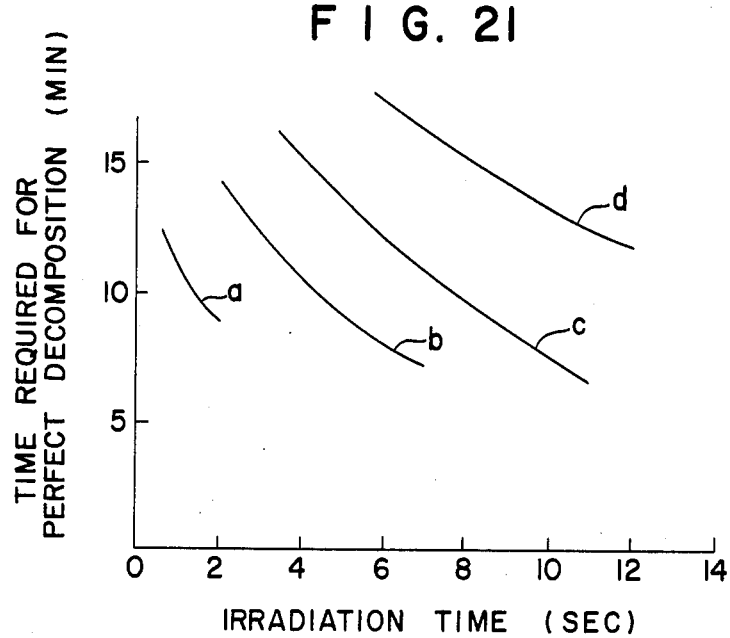
FIG. 21 is a graph showing relations among irradiation time, in seconds, of the microwave, the total time, in minutes, required for decomposition, and an interruption period.
Figure 23:
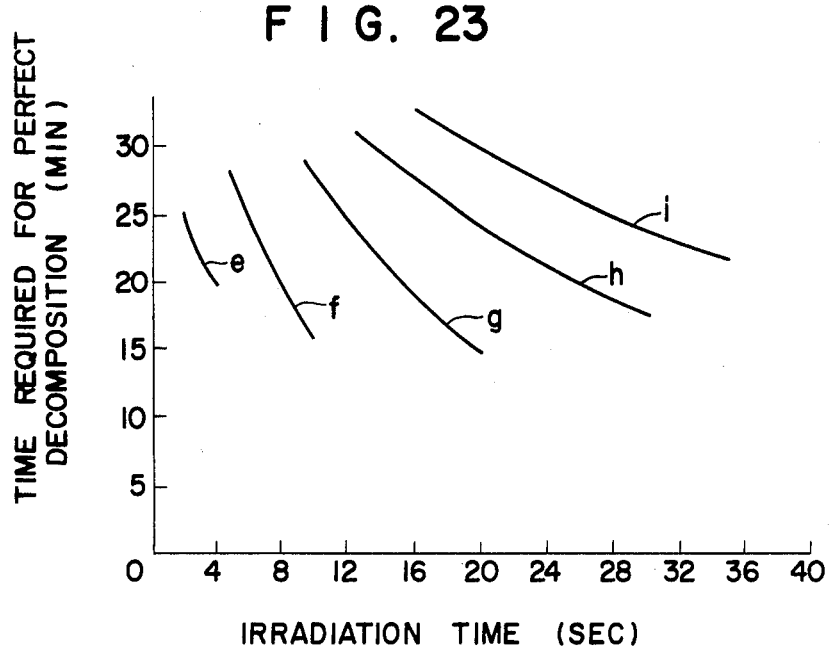
FIG. 23 is a graph showing the relation between the interruption period and the irradiation time.

The irradiation time for each operation and the interrupting period of the microwave of the apparatus described above will now be described. The term interruption period is used herein to mean the sum of the irradiated time and the not irradiated time. The irradiation time and the interruption period of the microwave have close relation as shown in FIG. 21 or 23. In FIG. 21, the ordinate represents the total time required for decomposing the sample in minutes, the abscissa the irradiation time in seconds of the microwave per one operation, and curves a through d correspond to interruption periods of 10, 20, 30 and 60 seconds respectively. Each curve shows that the decomposition time becomes longer as the irradiation time of the microwave decreases and vice versa. When the irradiation time exceeds a certain value, for example 7 seconds in curve b and 11 seconds in curve c foaming occurs at the early stage of decomposition, thus resulting in an overflow. For this reason, it is advantageous to decrease the irradiation time for the purpose of decreasing foaming but too short irradiation time extends the decomposition time. In other words, a long irradiation time is desirable to shorten the decomposition time but since too long irradiation time results in the overflow of the liquid to be decomposed due to foaming. Usually the irradiation time is selected to be in a range of 1 to 30 seconds, preferably 3 to 25 seconds.

Figure 22:
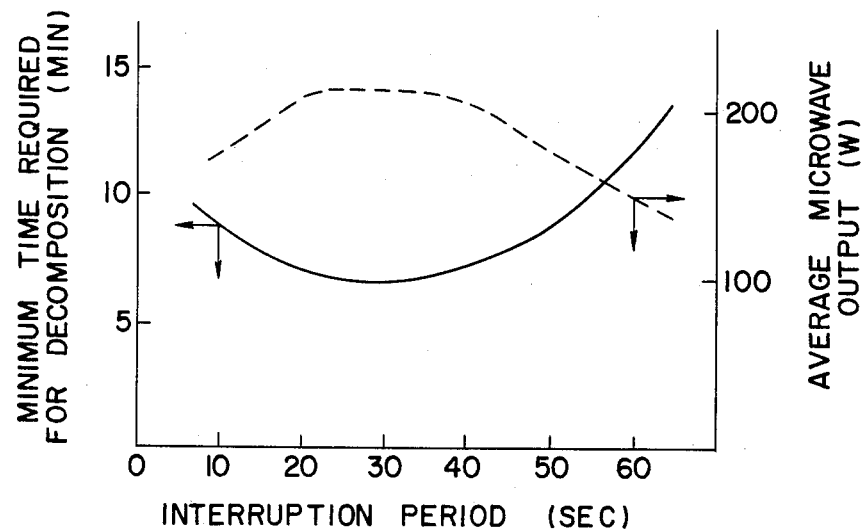
FIG. 22 is a graph similar to that of FIG. 21 but showing another example of the relations.

The interruption period of the microwave is closely related to the foaming at the early stage of the decomposition of the sample and since when the interruption period is short, it is impossible to sufficiently suppress the foaming, it is necessary to select the interruption period such that the irradiation of the microwave is stopped for an interval in which the foams disappear by cooling. As shown by FIG. 22, the interruption period is also related to the sample decomposing time in which a solid line curve shows the relation between the interruption period and the minimum time required for decomposition, that is the time required for completely decomposing the sample when the microwave is irradiated for a maximum permissible time (an interval in which an overflow of the liquid to be decomposed does not occur due to foaming) in each interruption period, whereas the dotted line curve shows the relation between the interruption period in seconds and the average microwave output in wats. As can be noted from FIG. 22, when the interruption period is shorter than 15 seconds, it is necessary to extremely shorten the irradiation time in order to obtain an interval sufficient to extinguish the foam. Conversely, with the interruption period longer than 45 seconds, although a long interval sufficient to extinguish the foam can be obtained, the irradiation time could not be made to be longer than 12 seconds due to the foaming. In each case, the average microwave output is decreased thus requiring longer decomposition time. For this reason, the interruption period of the microwave is limited to a range of 15 to 45 seconds, preferably 20 to 40 seconds.

Since the irradiation time is closely related to the interruption period in a manner described above, it is desirable to select them according to the following equation.

$$(S-5)\times 0.1 \leqq R \leqq (S-4)\times 0.73$$

in which R represents the irradiation time in seconds and S the interruption period in seconds, in this equation 15–45 seconds. More preferably $$(S+10)\times 0.1 \leqq R \leqq (S-6)\times 0.73$$

in which S is equal to 20–40 seconds.

FIG. 25 is a graph showing the relation expressed by these equations in which X represents an ordinary region, Y a preferred region and Z especially preferred range.

In certain kinds of the samples, the tendency of foaming decreases as the decomposition proceeds so that it is possible to gradually extend the irradiation time or decrease with time the interruption period.

Where the quantity of the sample is large, it is not necessary to firstly set the irradiation time and the interruption period in a manner as above described. For example, the sample may be continuously irradiated with the microwave in the early stage and then the irradiation time and the interruption period described above may be followed after the temperature of the sample has risen to a predetermined value.

As above described according to this invention, since the irradiation time and the interruption period of the microwave are selected to lie in specific ranges, it is not only possible to prevent foaming and bumping at the early stage of decomposition but also can reduce the decomposition time of the sample because of a large average irradiation quantity of the microwave. Accordingly, the decomposing apparatus of this invention is suitable for analyzing a nitrogen component or metal components contained in various samples.

Results of investigations regarding effective ranges of the irradiation time and the interruption period are as follows.

Experiment 1

An oscillator having a maximum microwave output of 700 W was used for microwave heating. 0.5 g of a powder of a dry plant leaf was put in a triangular flask having a bottom diameter of 60 mm. After dispersing the powder in 2 ml of water, 10 ml of concentrate nitric acid and 5 ml of concentrate perchloric acid were added and then the sample decomposing container was disposed in a microwave heater. Samples of the same composition were decomposed by varying the irradiation time and the interruption period of the microwave and the time at which the decomposed liquid is colored due to organics remaining in the liquid when the sample was completely decomposed, that is when the nitric acid has completely evaporated off was measured. The results obtained are shown in FIGS. 21 and 22. Alhtough a dry plant leaf was selected as a sample which foams vigorously, other samples, for instance, heavy oil, soil, biological samples, etc., also showed similar tendency.

Experiment 2

Figure 24:
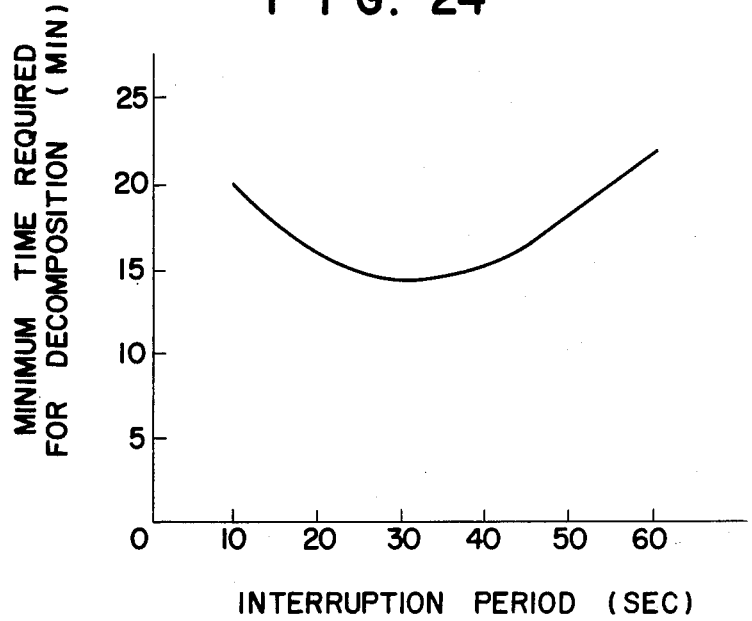
FIG. 24 is a graph showing another example of the relation between the microwave interruption period and respective interruption periods.

The same microwave heater and decomposing container as in experiment 1 were used and 0.5 g of activated carbon was used as a sample to be decomposed and put into the container. Then 20 ml of concentrated perchloric acid and 10 ml of concentrated sulfuric acid were added and the container was disposed in the microwave heater. Samples of the same composition were decomposed by varying the irradiation time and the interruption period of the microwave and the times necessary to completely liquefy the samples were measured. The results obtained are shown in FIGS. 23 and 24. In FIG. 23, curves e, f, g, h and i respectively correspond to the interruption periods of 10, 20, 30, 45 and 60 seconds.

As above described, according to this invention since respective sample decomposition containers are air tighly connected to the openings of the gas collector there is no fear of condensing the gas generated in the containers on the inner wall of the microwave heating container 3 and filling the same with white fume which makes it difficult to visually observe the decomposition state of the samples. Furthermore, when using the gas collector 12 since the sample decomposing containers 11 are connected to the gas collector with bayonet connectors the sample decomposing containers can be mounted with one touch operation, whereas when the gas collector 35 (FIG. 9) is used, since the sample decomposing containers 33 can be inserted into openings 40 from above the plate 36, their mounting and dismounting can be made easy. This construction of the gas collector 35 is simple and can be readily manufactured. A low blank value can be obtained as clean air is passed through the gas collector. Thus, the apparatus of this invention can assure high reproduceability, sensitivity and accuracy of the analysis.

What is claimed is:

1. A sample decomposing apparatus comprising;
a microwave heating container forming a chamber and having on one side thereof a transparent door that intercepts microwaves and a wall having a perforation formed therethrough;
a microwave controller for controlling microwaves radiated in said chamber;
a plurality of sample decomposing containers;
means defining a hollow gas collector having a first gas discharge opening and a plurality of inlet opening means therein for removably mounting and affixing to said collector means each of said plurality of sample decomposing containers each containing a sample to be decomposed to generate said first gas, said hollow gas collector being disposed in said microwave heating container;
means for introducing a second gas into the hollow gas collector from the exterior thereof; and
external suction means for removing said first and second gases from said gas collector through said perforation in the wall of said heating container.

2. The apparatus according to claim 1 wherein said microwave controller further comprises a pulse width control circuit for intermittently radiating said microwaves in said microwave heating containers at a predetermined interruption period.

3. The apparatus according to claim 2 wherein said microwave controller further comprises means for radiating said microwaves for 1 to 30 seconds at each interruption period of 15 to 45 seconds.

4. The apparatus according to claim 3 wherein said microwave controller further comprises means for radiating said microwaves at each interruption period for an interval expressed by an equation $$(S-5)\times 0.1 \leqq R \leqq (S-4)\times 0.73$$

where R represents a radiation time in seconds and S represents the interruption period in seconds.

5. The apparatus according to claim 1 wherein said means for introducing a second gas into said gas collector further comprises second gas inlet means formed in said gas collector.

6. The apparatus according to claim 5 further comprising means for connecting said second gas inlet means in said gas collector with the interior of said microwave heating container and a filter mounted within said second gas inlet means.

7. The apparatus according to claim 6 wherein said wall further includes a second perforation communicating with outside air or an external apparatus and said means for introducing said second gas further comprises means for connecting said second perforation to said second gas inlet means formed in said gas collector.

8. The apparatus according to claim 1 wherein an upper portion of each said sample decomposing container includes a gas inlet opening operatively connected with one of said plurality of gas collector inlet opening means for mounting said sample decomposing container.

9. The apparatus according to claim 1 further comprising means for removably mounting said gas collector in said microwave heating container.

10. The apparatus according to claim 1 wherein each of said plurality of inlet opening means for mounting said plurality sample decomposing containers is tapered outwardly whereby each of said plurality of sample decomposing containers is mounted on said gas collector by taper fitting.

11. The apparatus according to claim 1 further comprising bayonet coupling means for interconnecting each of said plurality sample decomposing containers to said gas collector.

12. The apparatus according to claim 1 wherein said plurality of inlet opening means are independently formed, and each of said plurality of inlet opening means is provided with a gas discharge opening.

13. The apparatus according to claim 12 wherein said gas collector further comprises a box shaped vessel having said plurality of inlet opening means formed therein for mounting said sample decomposing containers.

* * * * *